(12) United States Patent
Harlan et al.

(10) Patent No.: US 11,439,839 B2
(45) Date of Patent: Sep. 13, 2022

(54) HAND-HELD TREATMENT DEVICE USING LED LIGHT SOURCES WITH INTERCHANGEABLE EMITTERS

(71) Applicant: Acuity Innovation and Design, LLC, Scottsdale, AZ (US)

(72) Inventors: Laurence A Harlan, Scottsdale, AZ (US); Yoram Weiss, Cherry Hill, NJ (US)

(73) Assignee: Acuity Innovation and Design, LLC, Scottsdale, AZ (US)

( * ) Notice: Subject to any disclaimer, the term of this patent is extended or adjusted under 35 U.S.C. 154(b) by 27 days.

(21) Appl. No.: 15/673,309

(22) Filed: Aug. 9, 2017

(65) Prior Publication Data

US 2019/0046812 A1 Feb. 14, 2019

(51) Int. Cl.
*A61B 5/06* (2006.01)
*A61N 5/06* (2006.01)
(Continued)

(52) U.S. Cl.
CPC .............. *A61N 5/0624* (2013.01); *A61C 5/30* (2017.02); *A61C 5/40* (2017.02); *A61C 19/004* (2013.01);
(Continued)

(58) Field of Classification Search
CPC .............. A61N 5/0624; A61N 2005/05; A61N 2005/0606; A61N 2005/0626;
(Continued)

(56) References Cited

U.S. PATENT DOCUMENTS 5,611,793 A * 3/1997 Wilson .................. A61K 8/042
606/2
6,331,111 B1 * 12/2001 Cao .................... B23K 26/0096
433/29
(Continued)

FOREIGN PATENT DOCUMENTS

WO WO 2001 060280 A 8/2001
WO WO2016164238 A1 10/2016
WO WO2017015188 A1 1/2017

OTHER PUBLICATIONS

Salatec LED Mini Dental Curing Light downloaded Apr. 26, 2018 from https://www.dentalcompare.com/4653-Visible-Light-Curing-Units/38593-Satelec-Mini-LED-Curing-Light/.
(Continued)

*Primary Examiner* — Carl H Layno
*Assistant Examiner* — Michael J Lau
(74) *Attorney, Agent, or Firm* — Etherton Law Group, LLC

(57) ABSTRACT

A hand-held light treatment device configured with interchangeable emitter heads that are pre-programmed with desired treatment protocols and updated from a remote store of treatment protocols. The device comprises a handpiece, a plurality of emitter heads, and a base. The removable emitter heads each contain one or more treatment LEDs, a tracking light, a task light, a proximity sensor, and a control module. A tip is attached to the emitter head, either removably or integral therewith. In one embodiment, the tip is integral with the emitter head and emits light to the side of the device, perpendicular to the handpiece. The device is prohibited from emitting light when too far from a surface. Some embodiments have disposable tips of various shapes that attach to the emitter heads, which permits a single
(Continued)

device to direct the emitted energy at nearly any direction and be used in a variety of applications.

20 Claims, 13 Drawing Sheets

(51) Int. Cl.
  *A61C 13/15*   (2006.01)
  *A61C 5/30*   (2017.01)
  *A61C 5/40*   (2017.01)
  *A61N 5/00*   (2006.01)

(52) U.S. Cl.
  CPC .. *A61N 2005/005* (2013.01); *A61N 2005/063* (2013.01); *A61N 2005/0606* (2013.01); *A61N 2005/0626* (2013.01); *A61N 2005/0628* (2013.01); *A61N 2005/0644* (2013.01); *A61N 2005/0652* (2013.01); *A61N 2005/0659* (2013.01); *A61N 2005/0661* (2013.01); *A61N 2005/0662* (2013.01)

(58) Field of Classification Search
  CPC ...... A61N 2005/0628; A61N 2005/063; A61N 2005/0644; A61N 2005/0652; A61N 2005/0659; A61N 2005/0661; A61N 2005/0662; A61C 5/30; A61C 19/004
  USPC ..................................... 607/92, 101; 433/29
  See application file for complete search history.

(56) References Cited

U.S. PATENT DOCUMENTS

| | | | | |
|---|---|---|---|---|
| 6,466,198 B1* | 10/2002 | Feinstein | .............. | G06F 1/1626 345/158 |
| 6,468,077 B1* | 10/2002 | Melikechi | .............. | A61C 1/188 433/29 |
| 6,877,248 B1* | 4/2005 | Cross | .................... | D06F 58/203 34/275 |
| 7,168,122 B1* | 1/2007 | Riddell | .............. | A46B 15/0034 433/29 |
| 7,634,996 B2* | 12/2009 | Gaska | ..................... | A61L 2/10 128/207.14 |
| 7,988,688 B2* | 8/2011 | Webb | ................... | A61N 5/0618 128/898 |
| 8,656,744 B2* | 2/2014 | Kim | ...................... | D06F 37/267 68/901 |
| 9,585,549 B1* | 3/2017 | Elazar | ................ | A61B 1/00009 |
| 2002/0175896 A1* | 11/2002 | Vaananen | .............. | G06F 3/1407 345/158 |
| 2004/0156743 A1* | 8/2004 | Bornstein | ................. | C02F 1/30 604/20 |
| 2005/0050658 A1* | 3/2005 | Chan | .................... | A61C 17/221 433/29 |
| 2005/0123877 A1* | 6/2005 | Duret | .................... | A61C 19/004 433/29 |
| 2006/0047329 A1* | 3/2006 | Krespi | ................. | A61N 5/0603 607/86 |
| 2006/0088797 A1* | 4/2006 | Scott | .................... | A61C 19/004 433/29 |
| 2006/0283478 A1* | 12/2006 | Avila | .................... | A61C 15/041 132/321 |
| 2007/0038206 A1* | 2/2007 | Altshuler | ........... | A46B 15/0036 606/20 |
| 2007/0185553 A1* | 8/2007 | Kennedy | .............. | A61N 5/0616 607/100 |
| 2007/0223984 A1* | 9/2007 | Schweers | ............. | G06F 1/1664 400/486 |
| 2007/0259309 A1* | 11/2007 | West | .................... | A61C 19/004 433/29 |
| 2008/0215123 A1* | 9/2008 | Maricle | .............. | A61N 5/0617 607/89 |
| 2008/0221558 A1* | 9/2008 | Becker | ................. | G02B 6/3895 606/10 |
| 2008/0276393 A1* | 11/2008 | Russell | ................ | A61N 5/0624 15/105 |
| 2010/0121419 A1* | 5/2010 | Douglas | ............... | A61N 5/0616 607/90 |
| 2010/0291502 A1* | 11/2010 | Knight | ............... | A61C 17/0202 433/29 |
| 2011/0052123 A1* | 3/2011 | Barnes | ................. | G02B 6/3888 29/525.05 |
| 2011/0123958 A1* | 5/2011 | Piergallini | .............. | A61P 17/02 604/20 |
| 2011/0144410 A1* | 6/2011 | Kennedy | .............. | A61K 31/327 600/2 |
| 2011/0162155 A1* | 7/2011 | Wai | .................... | A46B 15/0002 15/4 |
| 2011/0224584 A1* | 9/2011 | Pryor | .................. | A61N 5/0603 601/15 |
| 2011/0301671 A1* | 12/2011 | Lytle | .................... | A61N 5/0613 726/5 |
| 2012/0156637 A1* | 6/2012 | Benz | .................... | A61C 19/004 433/29 |
| 2013/0052607 A1* | 2/2013 | Gersh | .................. | A61C 19/004 433/27 |
| 2013/0177865 A1* | 7/2013 | Ostler | ................. | A61C 1/0046 433/29 |
| 2014/0074193 A1* | 3/2014 | Luzon | .................. | A61B 18/203 607/88 |
| 2014/0078086 A1* | 3/2014 | Bledsoe | ................ | G06F 3/0488 345/173 |
| 2014/0202493 A1* | 7/2014 | Zelickson | ............... | F16H 25/18 134/6 |
| 2014/0316492 A1* | 10/2014 | Min | ....................... | A61M 21/02 607/91 |
| 2014/0347223 A1* | 11/2014 | Hyde | ................. | H04B 7/15507 342/385 |
| 2015/0030989 A1* | 1/2015 | Soukos | ................ | A61N 5/0603 433/29 |
| 2015/0072144 A1* | 3/2015 | Bishop | ................. | C09D 175/16 65/432 |
| 2015/0157119 A1* | 6/2015 | Barnes | ................. | A61N 5/0603 134/6 |
| 2016/0038762 A1* | 2/2016 | Lin | ....................... | A61N 5/0603 433/29 |
| 2016/0074144 A1* | 3/2016 | Peterson | .............. | A61C 19/004 433/29 |
| 2017/0035506 A1* | 2/2017 | Waclawik | .............. | A61B 18/20 |
| 2017/0056130 A1* | 3/2017 | Cannon | ................ | A61C 19/004 |
| 2017/0080251 A1* | 3/2017 | Yehezkel | ................ | H04M 1/17 |
| 2017/0128740 A1* | 5/2017 | Stephens | .............. | A61N 5/0616 |
| 2017/0189711 A1* | 7/2017 | Shur | .................... | A61N 5/062 |
| 2017/0197090 A1* | 7/2017 | Newman | ................ | A61N 5/062 |

OTHER PUBLICATIONS

Aita H, et al., Ultraviolet light-mediated photofunctlonallzatlon of titanium to promote human mesenchymal stem cell migration, attachment (abstract), Acta Biomater. 2009.

Att W, et al, The effect of UV-photofunctlonallzatlon on the time-related bioactivity of titanium and chromlum-cobalt alloys (abstract), Biomaterials. 2009.

Coohill TP et al, Overview of the Inactivation by 254 nm ultraviolet radiation of bacteria with particular relevance to biodefense (abstract), Photochem Photobiol. Sep.-Oct. 2008.

Dai T et al, Ultraviolet C light for Acinetobacter baumannll wound Infections In mice: potential use for battlefield wound decontamination? (abstract) J Trauma Acute Care Surg.

Dai T et al, Ultraviolet C Irradiation: an alternative antimicrobial approach to localized infections? (abstract) Expert Rev Anti Infect Ther. 2012.

Hori et al, Ultraviolet light treatment for the restoration of age-related degradation of titanium bioactivity (abstract) Iot J Oral Maxjllofac Implants. Jan.-Feb. 2010;25(1):49.

Sugita et al, Role of photofunctlonallzation in mitigating Impaired osseolntegration associated with type 2 diabetes In rats (abs Int J Oral Maxillofac Implants. Nov. 2014-Dec.

(56) References Cited

OTHER PUBLICATIONS

Yamazaki etal, Ultravlolet-C Irradiation to titanium Implants Increases perl-Implant bone formation without Impeding mineralization . . . (abstract) Acta Odontol Scand. 2015.

* cited by examiner

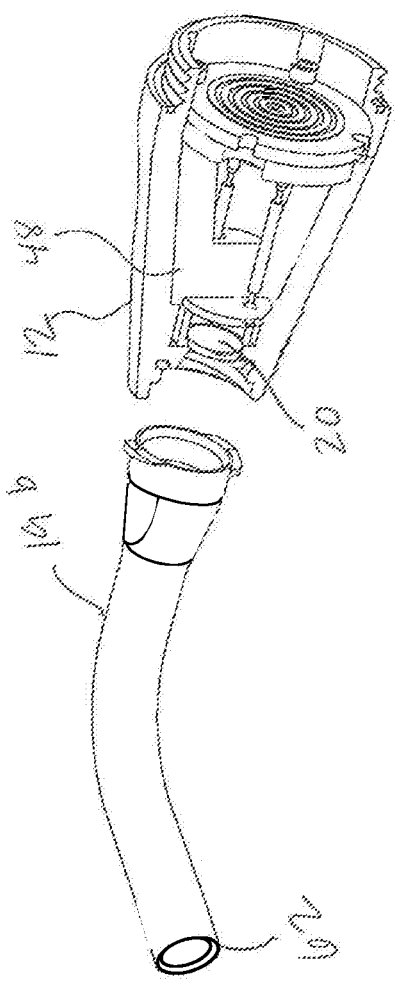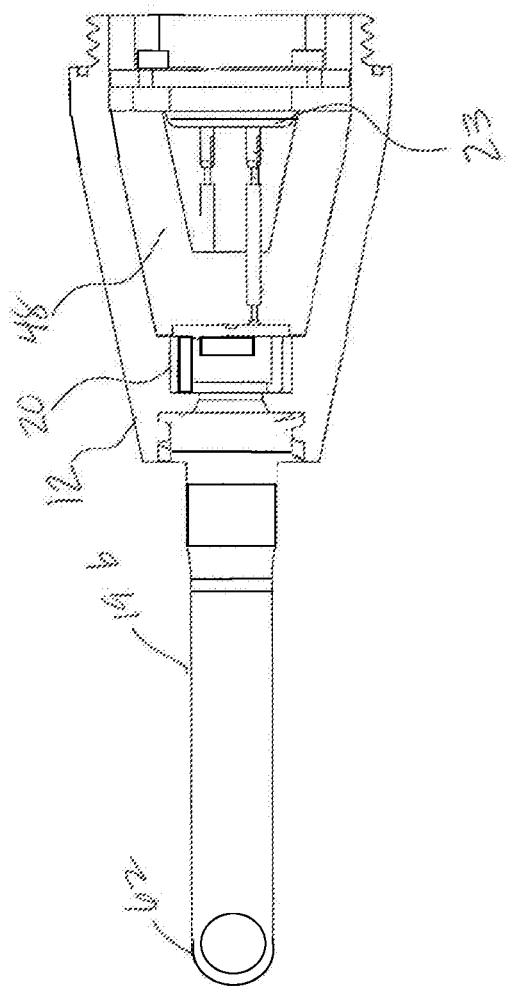
FIG. 8A
FIG. 8B

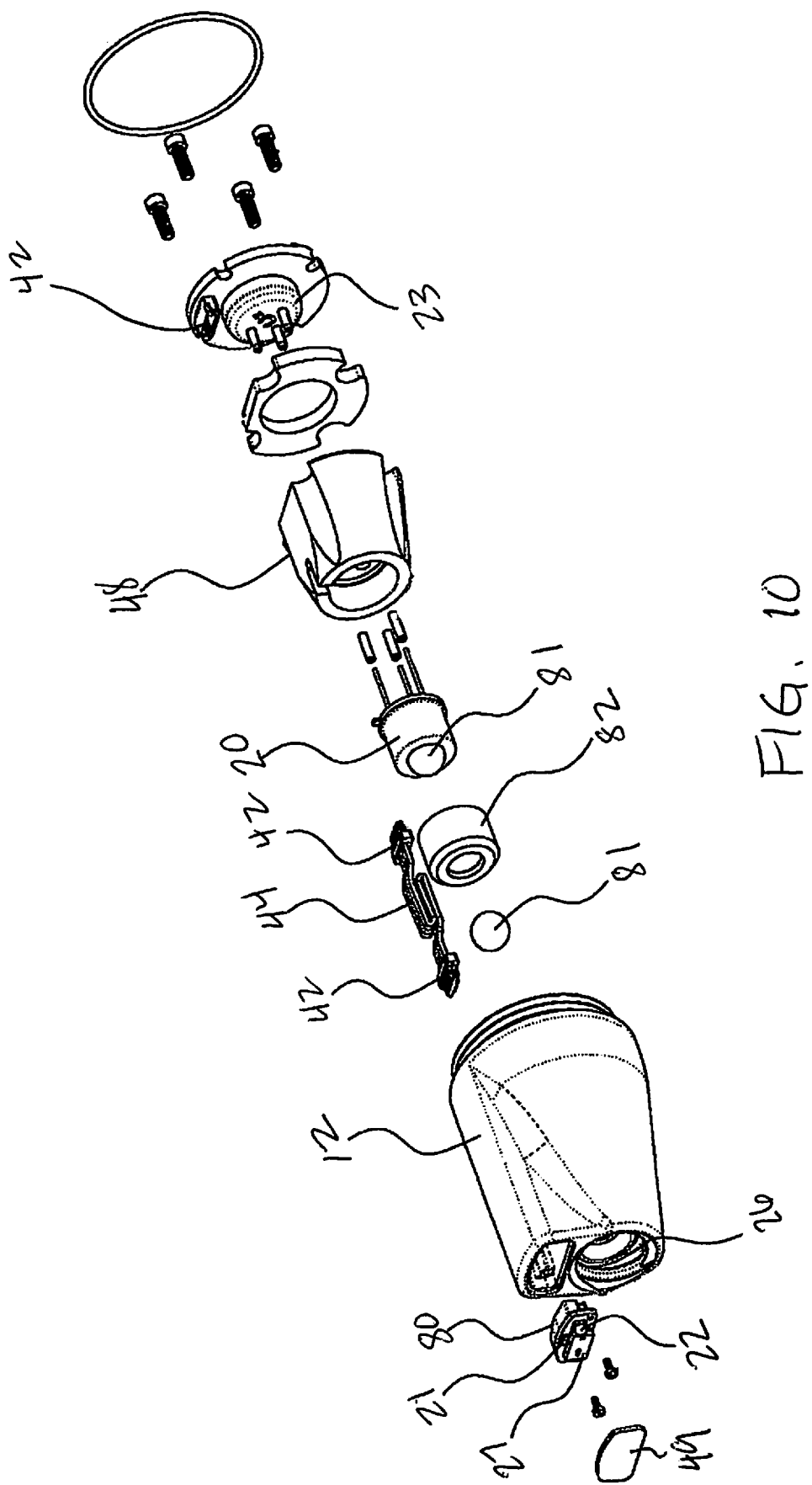

a round or oval cross section, but may take on any shape that enables a secure grip. The housing 14 may be made in one piece or several pieces that fit together. FIG. 1 shows a housing 14 with two portions 14a and 14b. A rechargeable battery 15 resides in the housing 14, along with a display 16.

HAND-HELD TREATMENT DEVICE USING LED LIGHT SOURCES WITH INTERCHANGEABLE EMITTERS

FIELD OF INVENTION

This invention relates generally to handheld devices that deliver light treatment for applications in dentistry and medicine. This invention relates particularly to a multifunction device with interchangeable emitter heads capable of emitting a broad range of wavelengths, individually and independently controlled, with disposable tips of various shapes for use in multiple applications.

BACKGROUND

Light-emitting devices are popular in dentistry and medicine for invasive and non-invasive therapeutic treatments, sanitization, and product curing applications. Each of these applications requires a different duration, intensity, area of treatment, and wavelength of applied light.

Although ultraviolet radiation can be harmful to humans, it can also be beneficial. For example, it is known that electromagnetic radiation in the UV-C range, about 100-280 nm, kills certain bacteria and other microorganisms. Consequently UV-C can be applied to surfaces to disinfect them or, since UV-C may selectively inactivate organisms while preserving the viability of mammalian cells, applied to live tissue to kill or even prevent bacterial infections in wounds.

Today most orthopedic and dental implants are made of titanium alloys. Treating the implants with UV-C increases their bioactivity. Increased bioactivity in turn increases osseointegration, which helps the implants stay in place after implantation and not be rejected by the body. UV-A and blue light are used to cure certain resins, such as synthetic resins that are used in dentistry as restorative material or adhesives.

It would be beneficial to use UV-C radiation in dental and orthopedic surgeries, but until recently UV-C was produced by relatively large bulbs or lamps that got hot when operating and rapidly degraded in their output. The UV light was directed to the desired location by transmitting it through optical fibers. This meant the wand through which the light was emitted was tethered to a base containing the bulb, power source, and often a fan or heat sink to keep the device cool. This made the application of UV-C light to tissue and surfaces in small spaces, such as those in orthopedic surgery openings and dental surgery in the mouth, unwieldly.

Therefore there is a need to provide a light-emitting device that disinfects mouth tissue, cures resins, reactivates Ti implants and that is convenient to use. There is also a need to provide a device that emits UV light from a hand-held device that is not tethered to a base. The device should be capable of delivering a variety of treatment parameters for a variety of applications.

SUMMARY OF THE INVENTION

This hand-held light treatment device is configured with interchangeable emitter heads that can be pre-programmed with desired treatment protocols, which can be changed or updated from a remote store of treatment protocols. The device comprises a handle, a plurality of emitter heads, and a base. In one embodiment the device comprises removable emitter heads each containing one or more treatment LEDs, a tracking light, a task light, a proximity sensor, and a control module. A tip is attached to the emitter head, either removably or integral therewith. In one embodiment, the tip is integral with the emitter head and emits light to the side of the device, perpendicular to the handle. Some embodiments have removable, disposable tips of various shapes that attach to the emitter heads, which permits a single device to direct the emitted energy at nearly any direction and be used in a variety of applications. The sensor enables several safety features, such as prohibiting UV light from being emitted when the device is too far from a surface, isn't moving, or after a predetermined period of time. In a preferred embodiment the device uses UV-C, UV-A and blue light energy, but can range in output from 200-1400 nm.

BRIEF DESCRIPTION OF THE DRAWINGS

FIG. 8A is a perspective cut-way view of an axial emitter with a perspective view of a detached disposable tip.

FIG. 8B is a side view of the device in FIG. 8A with the tip attached.

FIG. 10 is an exploded view of an axial emitter.

DETAILED DESCRIPTION OF THE INVENTION

This invention is a light delivery platform with multifunction modular and interchangeable emitter heads and disposable tips, used for a variety of applications. The device comprises generally a handle 11, a plurality of emitter heads 12, and a base 13.

Figure 1:
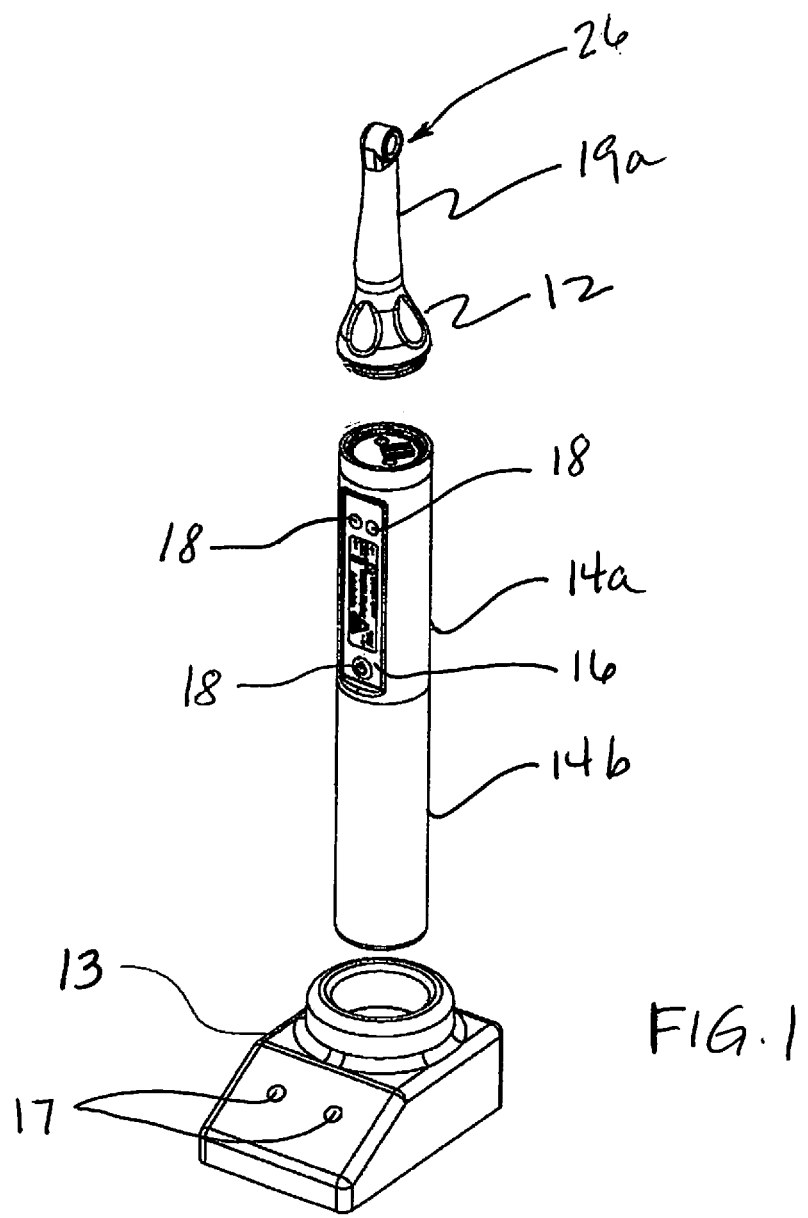
FIG. 1 is a partially exploded view of a side emitter embodiment of the device.

The handle 11 comprises a housing 14 defining an interior cavity which is shaped to be easily retained in a user's hand. Preferably the housing 14 is an elongated hollow tube with a round or oval cross section, but may take on any shape that enables a secure grip. The housing 14 may be made in one piece or several pieces that fit together. FIG. 1 shows a housing 14 with two portions 14a and 14b. A rechargeable battery 15 resides in the housing 14, along with a display 16.

Figure 2:
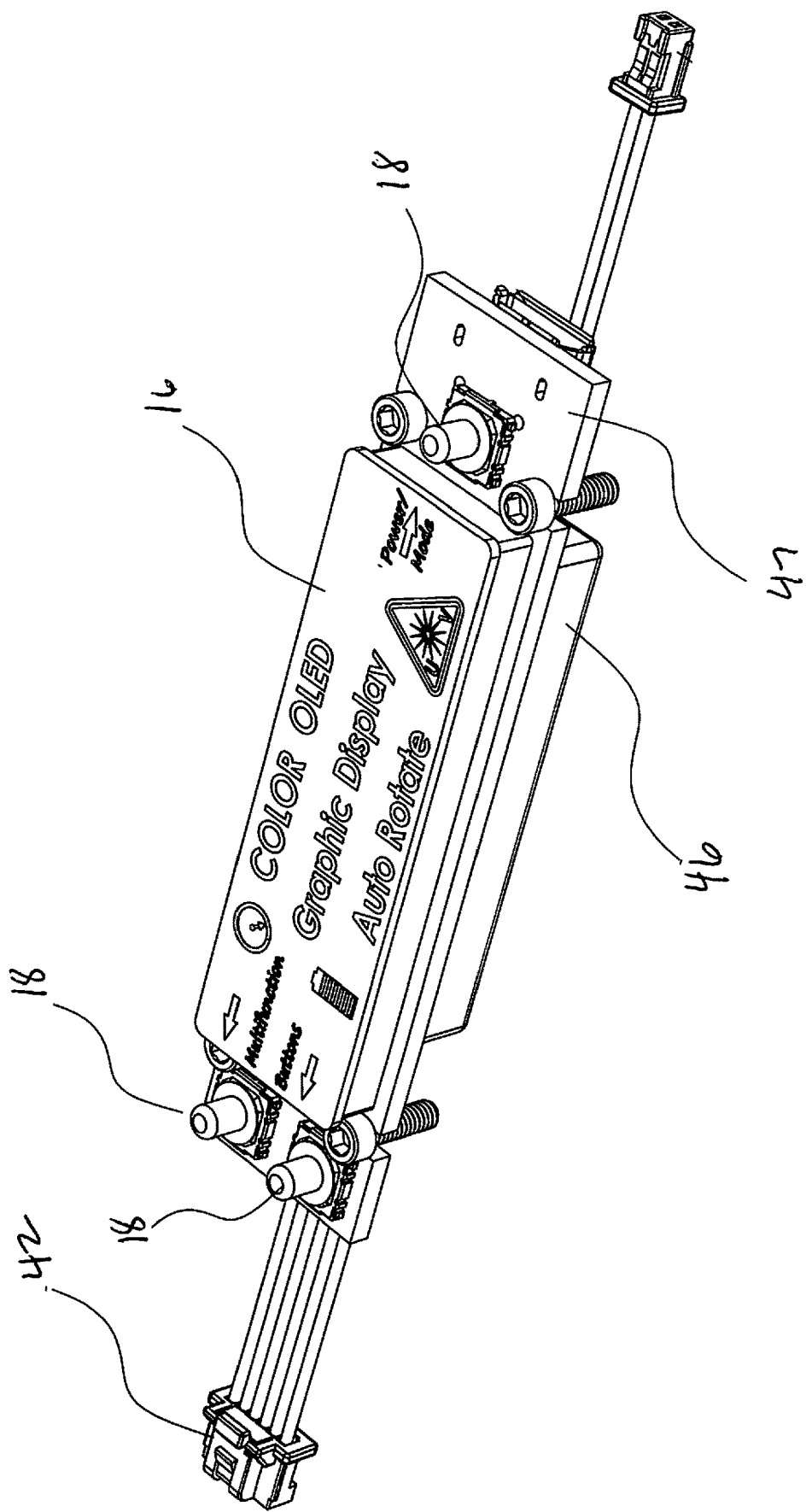
FIG. 2 is a perspective view of the display.

The display 16 is preferably an organic light-emitting diode (OLED) with an alphanumeric and graphic display. See FIG. 2 which shows an exemplary display of the words "COLOR OLED Graphic Display Auto Rotate" and other symbols. The display 16 is driven by a display driver and microprocessor housed in housing 46 and is in electrical communication with a display printed circuit board (PCB)

47. The display 16 may also have buttons 18 or switches, mechanical or electronic, which enable the user to enter input and scroll through data. The display 16 can be read by the user whether holding the device in his right hand or his left hand, which is accomplished by using a gyroscope, particularly a MEMS device, that auto-rotates what is displayed on the screen the screen so that it is oriented properly for viewing. A preferred inertial module is an always-on 3D accelerometer and 3D gyroscope, such as the LSM6DSL available commercially from STMicroelectronics.

One end of the handle 11 mates with a base 13. The base 13 is connected to mains power and is in electrical communication with the battery 15 to recharge it when the handle 11 is seated in the base 13. Typically the base 13 provides a stable stand to dock the handle 11 in vertically. The base 13 may have indicator lights 17 for indicating when it is charging the battery 15 and when the battery 15 is fully charged. Due to the rechargeable battery 15 and the on-board UV sources, the handle 11 is cordless. That is, when the handle 11 is removed from the base 13, it is untethered.

The other end of the handle 11 mates with a removable emitter head 12 from which the treatment energy and tracking light are emitted through an emission aperture 26. Light emitting diodes (LEDs), sensors, and control modules are housed in the emitter head 12. The emitter head 12 contains at least one LED 20 for emitting the treatment light. The treatment LED 20 may emit any wavelength, from UV-C to infrared, roughly a range of 200-1400 nm. Recent improvements in the manufacturing of light emitting diodes have made UV LEDs commercially available. They have many advantages over traditional mercury vapor bulbs including smaller size, longer lifespan, improved efficiency, less heat, and lack of significant time-related energy output degradation. In one embodiment, the treatment LED 20 emits energy in the UV-C range, about 100-280 nm or in the UV-A range, about 315-400 nm. Commercial UV LEDs have a small spread of emitted wavelengths around a nominal wavelength, with the desired wavelength within the spread from nominal. In a preferred embodiment the treatment LED 20 emits light at about 254 nm nominal. In another embodiment, the LED may emit energy more broadly across the UV spectrum, for example from about 260 nm-410 nm. Multiple emitter heads 12 may be provided to cooperate with the handle 11, each one with at least one treatment LED 20 having a different wavelength and having different operational parameters. In this manner a single device can be used for multiple applications, such as sanitization, disinfection, sterilization, curing, increasing bioactivity, wound treatment, or ablation, by exchanging one of the interchangeable emitter heads for another.

The emitter head 12 contains a second LED 21 for emitting visible light to enable the user to track where the treatment light is landing. The tracking LED 21 may emit any wavelength in the visible range, roughly 390 to 700 nm. Typically the visible light is in the blue range, about 450-495 nm. Optionally, the emitter head 12 contains a third LED 22 for emitting visible light used as ambient or task lighting, to more easily see the treatment area. Typically the task light LED 22 emits broadband white light. The device may have one or more optical devices to shape or manipulate the emitted energy, such as a lens or a collimator. The light may be transmitted through to the end of the tips by optical fiber. Optionally, the emitter head 12 contains three additional LEDs, for a total of six, each typically of a different wavelength. Each LED is controlled individually, thus the entire array can provide a broadband mix of wavelengths.

The emitter head 12 contains one or more sensors that are in communication with a control module 23, as discussed below. The sensors prohibit the emission of UV energy under certain conditions. The sensor may be an accelerometer, which prohibit emissions when the handle 11 stops moving, which helps prevent the device from emitting hazardous treatment emissions when the device is at rest in the base 13 or on a counter. The sensor may be a timer or clock, which prohibits emissions upon the expiration of a predetermined time period. This helps prevent the surface being treated from over-exposure of the treatment light. As explained above, the sensor may be an inertial module to sense position to effect auto-rotation. In addition to the inertial module, a capacitive touch sensor may be in communication with the control module. The combined sensing capabilities of the inertial module and capacitive touching sensors can be utilized for varieties of operational and safety features. For example, they can recognize when the device is touched, even if the device is not moved from its resting position, so it can "wake up" from a standby state and turn on the display. They can detect the orientation of the device to detect movement to provide auto "on" state or shutoff for safety measures, as well the aforementioned autorotation of the display.

Temperature sensors may be imbedded on the heatsinks of the LEDs and the battery to protect these components from overheating. The battery's temperature sensing circuitry will provide overheating protection in both charging state and rapid discharging in case of a failure or accidental short circuit. The LED temperature protection circuit will scale back the power to the LEDs or turn the LEDs off to keep the device's temperature within the safe operating parameters.

In a preferred embodiment, one sensor is a proximity sensor 27, which measures the light reflected back to it. The proximity sensor is a LIDAR sensor, and more preferably a time-of-flight (TOF) sensor, as opposed to a scanning sensor. A preferred sensor is a combination a proximity, gesture and ambient light sensor which is available commercially, such as the VL6180X from STMicroelectronics. LIDAR resolves distance by measuring the time of flight of a light signal between the sensor and the surface for each point of the image. The time-of-flight LIDAR sensor captures the treatment area light pulse, as opposed to point-by-point with a scanning LIDAR system. By measuring the light reflected back to the unit, the proximity detector serves as a safety control shutting the unit off when it is too far away from the target to be effective as well as preventing the device from emitting potentially hazardous treatment emissions to anywhere but the surface to be treated. The light sensor can detect differences between light reflected back from teeth enamel vs. tissue, permitting treatment parameters to be adjusted accordingly.

A control module 23 is housed in the emitter head 12. The control module 23 is typically a programmable logic device (PLD) or microprocessor and is in electrical communication with the LEDs, the sensors, the display 16, the battery 15, and a memory device as discussed more below. The control module 23 is able to identify which emitter head 12 is connected to the handle 11 and thereby controls the operational parameters of the device per the attached emitter head 12. Operation parameters include intensity (power per unit area such as W/cm2), ramp-up/ramp-down, wavelength mix, duration of each emission from the LEDs, how often the emissions may occur, and whether the emissions from the treatment emission and tracking light are on concurrently. The ramp-up feature is safety measure. When the device is first turned on, the light will slowly ramp up to full brightness rather than turn on instantaneously at full brightness. This way, if a user turns the device on while looking directly into the LED, it will give ample of warning and plenty of time to look away or turn the device away before it reaches full brightness. Some emitter heads have multiple protocols stored therein. The user can cycle through the options using the buttons 18 on the display 16.

By having interchangeable emitter heads, a user can have an assemblage of pre-programmed protocols at the ready and use whichever one is appropriate for a given patient, without having to program the device at the time of need. Another benefit of pre-programmed emitted heads is that one pre-programmed head can be used with one protocol and a second pre-programmed head can be used with a second protocol on a given patient, again without having to stop and program the device.

The emitter head 12 also contains a memory device 25 for storing operational parameters, and is in electrical communication with the control module 23 or incorporated therewith. Preferably the memory device 25 is programmable, as opposed to having fixed memory, which will suffice in certain configurations. Operational parameters and treatment protocols formed therefrom are customizable for different applications and different patients. The operational parameters are changed by local selection, using menu-driven multi-function buttons 18 on the display 16 which in turn instructs the control module 23 or memory device 25, or by loading new operational parameters from an external device such as a phone app, computer, tablet, or other computing device, either wirelessly or via hard-wiring with a built-in connector such as a USB port, as known in the art. The built-in connector may be in the base 13 or in the handle 11. Because the memory is programmable, future hardware and software can be forward and backward compatible.

In addition to storing protocols, the memory stores data from operating records and device parameters. For example, when applied to an individual patient, the memory stores the history of the protocols administered per treatment, total number of treatments, and cumulative time and amount of radiation. The memory stores device parameters such as the history of total number of hours of operation for LEDs, the number of charges for the battery to provide notification of end-of life or service requirements, and meters temperatures for warranty and servicing determinations.

The stored data is locally retrievable on the display 16 and may also be downloaded to an external device wirelessly or via hard wiring with a built-in connector when docked into the base 13.

Figure 3:
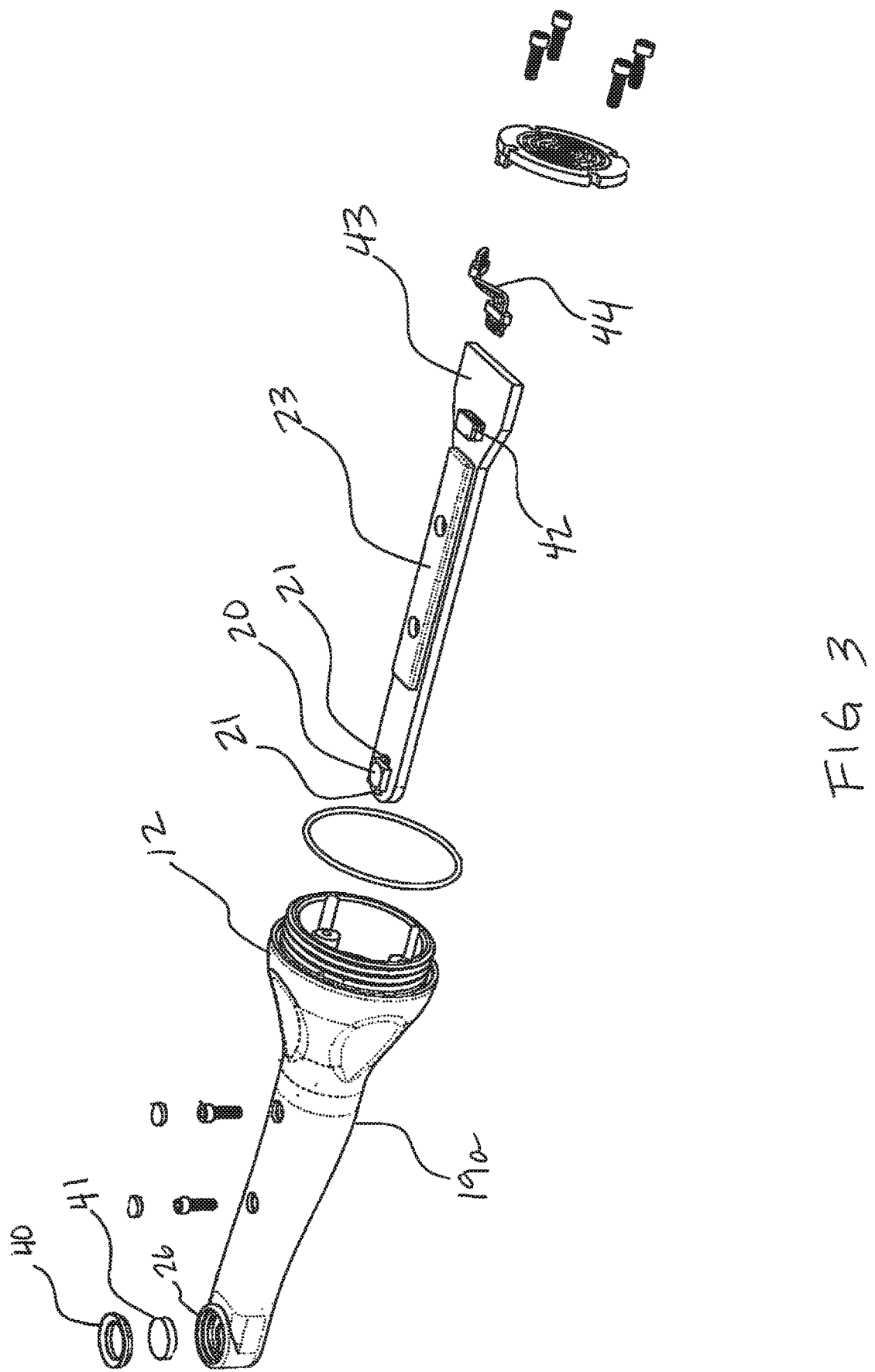
FIG. 3 is an exploded view of a side emitter.

The emitter head 12 has a tip 19 through which the treatment light is directed to the desired location and emitted through the emission aperture 26. As shown in FIGS. 1, 3, and 4-5, the tip 19a can be integral with the emitter head 12 FIG. 3 shows one embodiment of a tip 19a integral with the emitter head 12. A lens 41 is secured in the tip 19a by a lens retaining ring 40. Typically lens 41 is an uncoated UV plano-convex lens. Two tracking LEDs 21, a treatment LED 20, and a control module 23 are attached to and in electrical communication with an emitter printed circuit board (PCB) 43. The emitter PCB 43 is electrically connected to the display 16 and battery 15 in the handle 11 by attaching the wiring harness 44 to the connector 42 and a mated connector in the handle (not shown).

Figure 4:
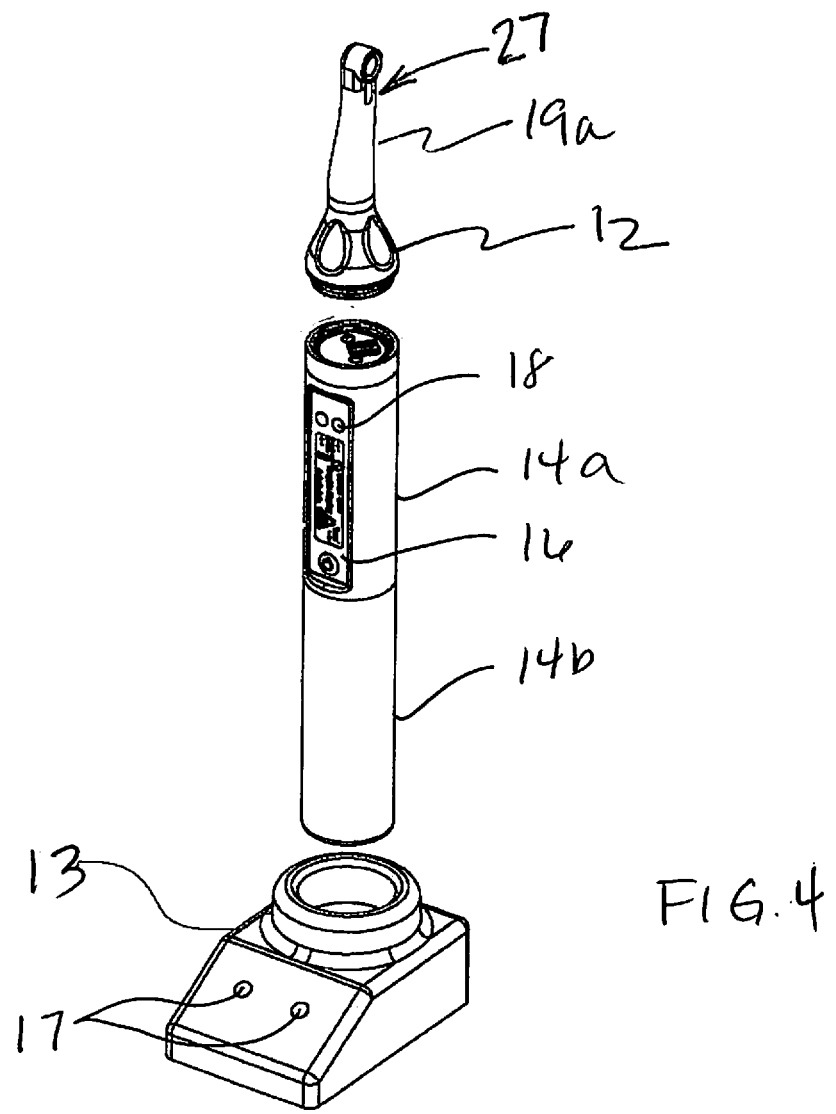
FIG. 4 is a partially exploded view of a side emitter embodiment of the device, with a proximity sensor and a task light.
Figure 5:
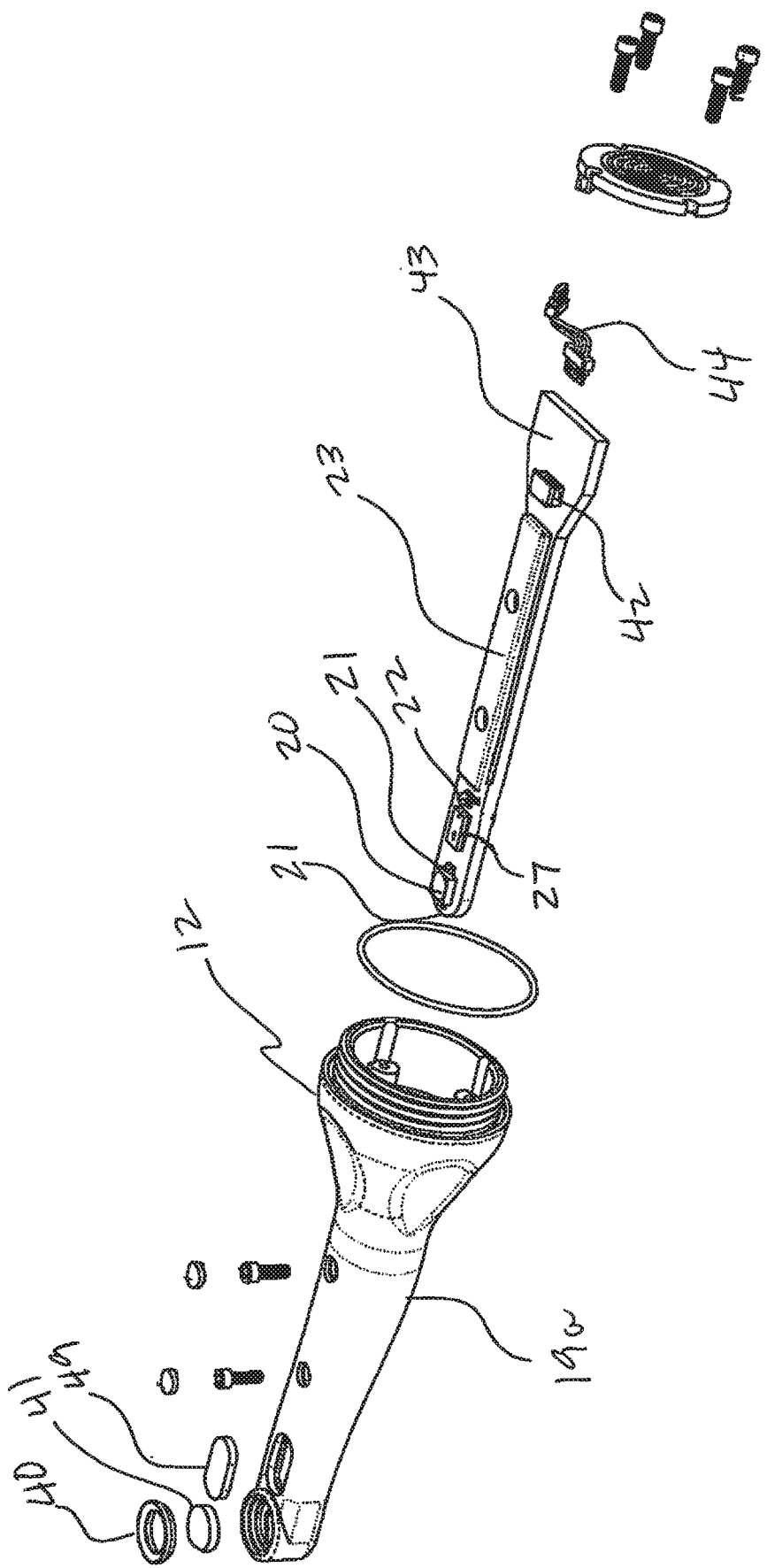
FIG. 5 is a partially exploded view of a side emitter embodiment of the device, with a proximity sensor and a task light.
Figure 6:
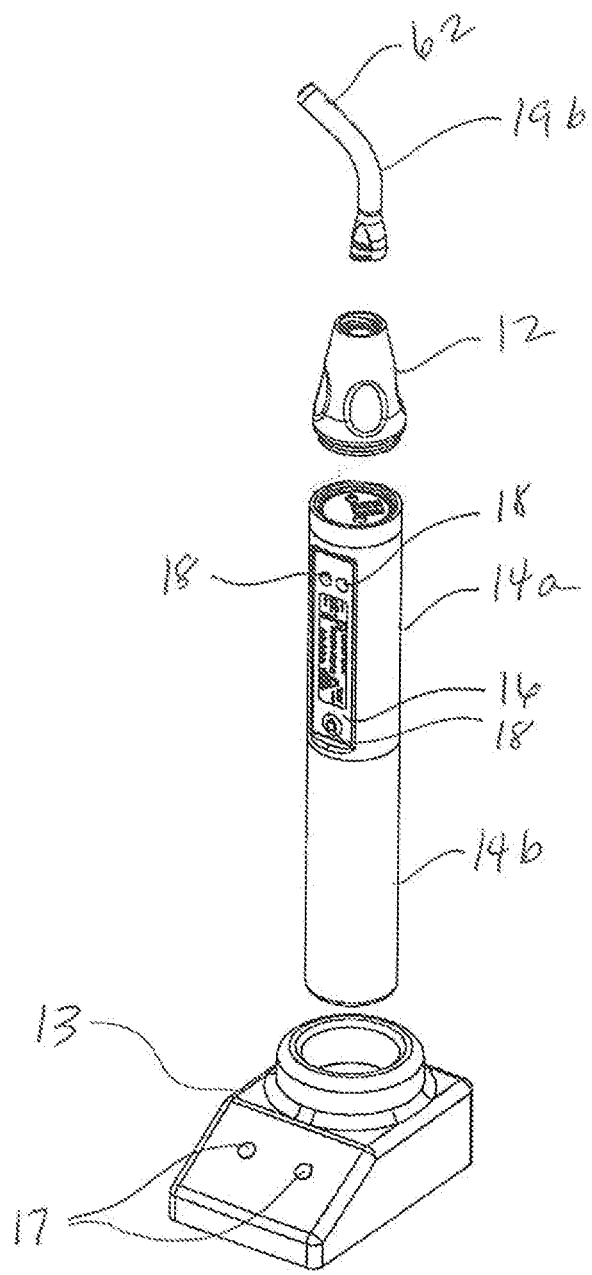
FIG. 6 is a partially exploded view of an axial emitter embodiment of the device with a removable tip.
Figure 7:
FIG. 7 is an exploded view of an axial emitter.
Figure 9:
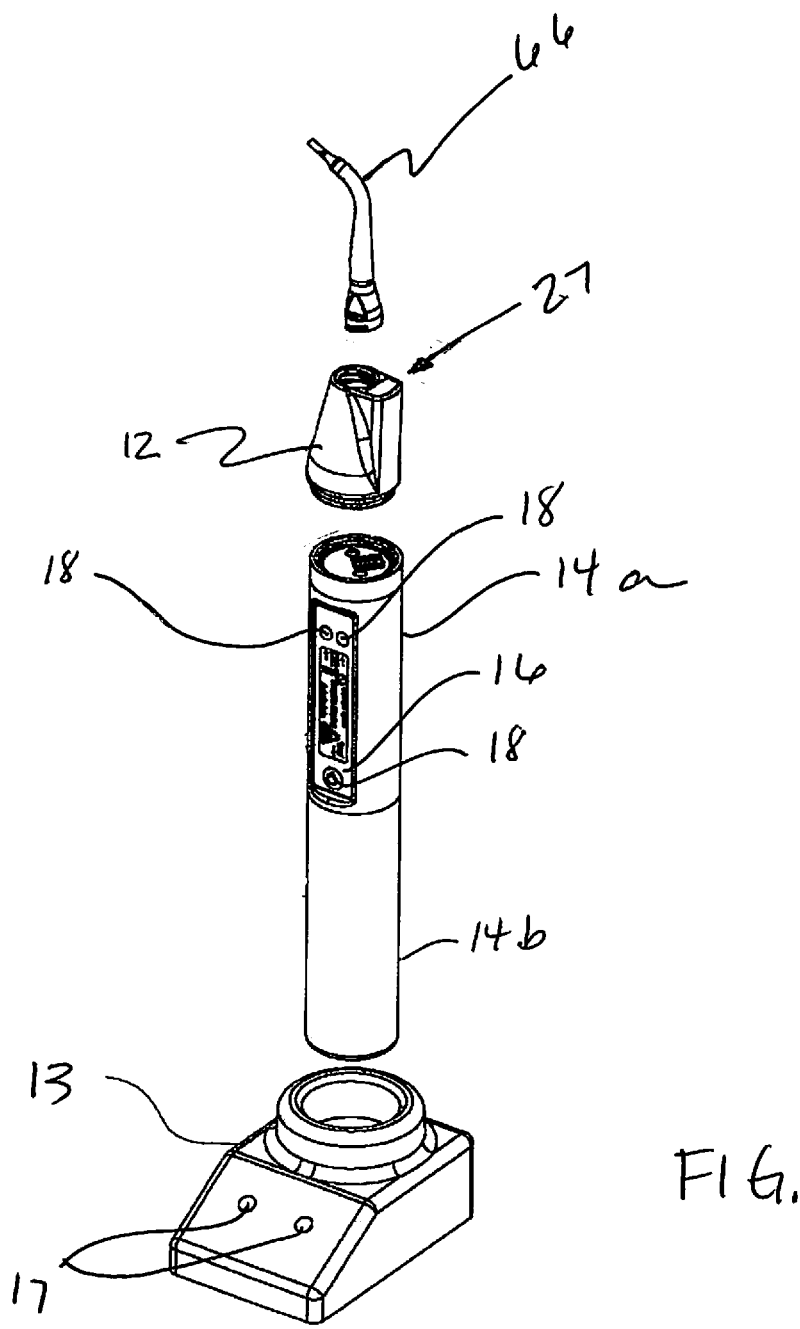
FIG. 9 is a partially exploded view of an axial emitter embodiment of the device with a removable tip, a proximity sensor and a task light.
Figure 11A:
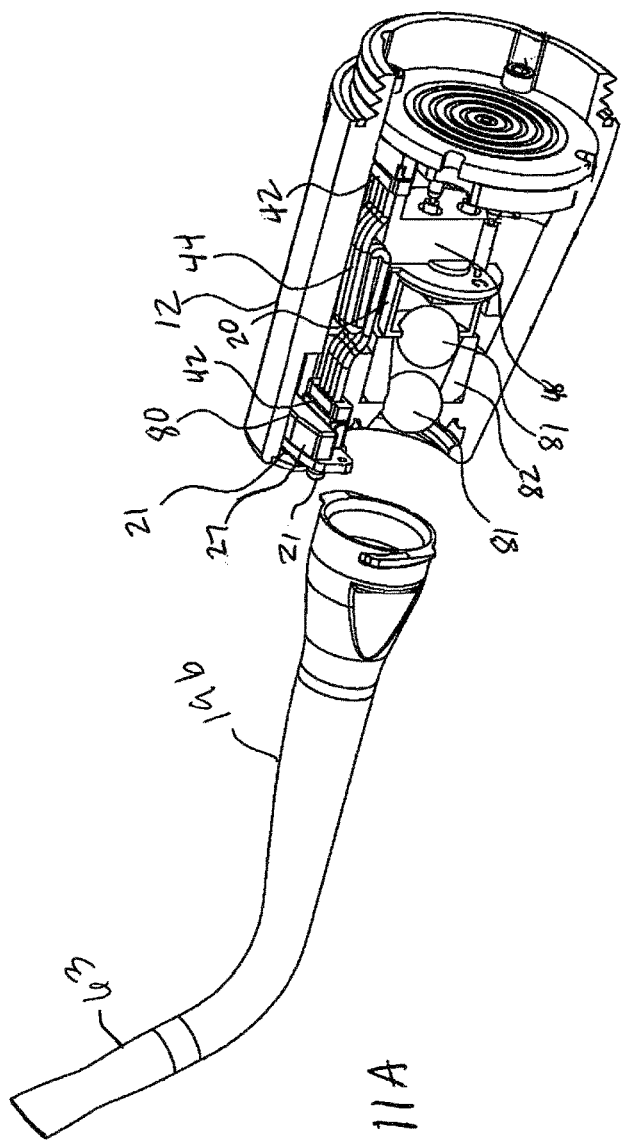
FIG. 11A is a perspective cut-way view of an axial emitter with a perspective view of a detached disposable tip.
Figure 11B:
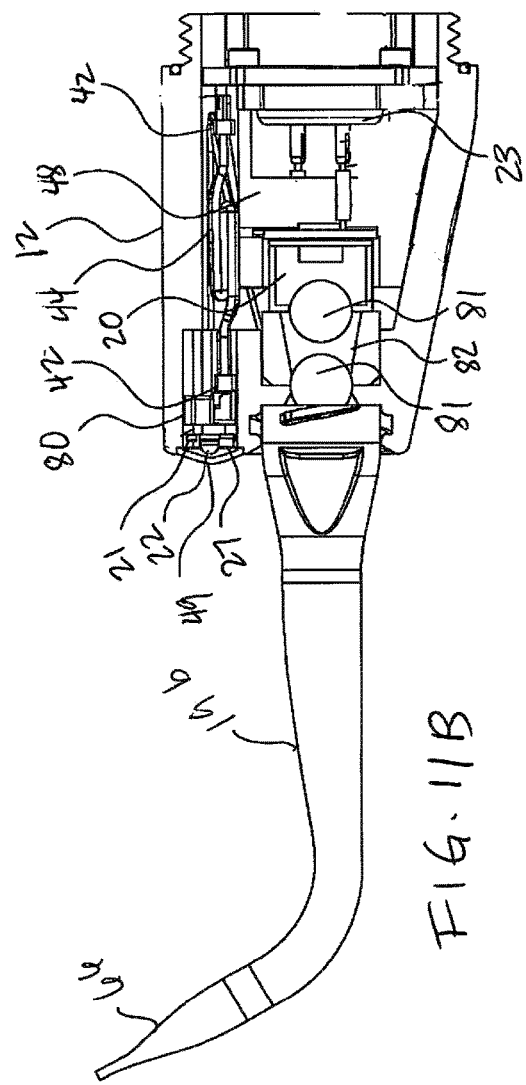
FIG. 11B is a side view of the device in FIG. 11A with the tip attached.

FIGS. 4 and 5 show another embodiment of a tip 19a integral with the emitter head 12. As in FIG. 3, a lens 41 is secured in the tip 19a by a lens retaining ring 40. However adjacent to the emission aperture 26, is a proximity sensor 27 which may be protected by a sensor cover 49. Two tracking LEDs 21, a treatment LED 20, and a control module 23 are attached to and in electrical communication with an emitter printed circuit board (PCB) 43. The emitter PCB 43 is electrically connected to the display 16 and battery 15 in the handle 11 by attaching the wiring harness 44 to the connector 42 and a mated connector in the handle (not shown).

In a preferred embodiment, the tip has a longitudinal axis co-axial with the longitudinal axis of the handle 11 and an aperture configured such that the UV energy emitted from the device is perpendicular to the longitudinal axis of the handle 11. This side-emitter arrangement has the advantage of enabling the longitudinal axis of the handle 11 be parallel to the treated surface. See FIGS. 1-4. This is particularly advantageous for applying UV energy to a tooth or other surface in a patient's mouth. For example, a side-emitter arrangement emitting UV-C with a proximity sensor can be used to sterilize tissue pre-surgery, to treat infected tissue, to sanitize or sterilize the surface of dental cavity and crown preparations prior to the placement of dental restoratives or the cementation of crowns, bridges, inlays and onlays. This process may be performed while using a rubber dam to protect the soft tissue of the mouth. In another example, the side emitter emitting UV-C with a proximity detector can be used for medical treatment of staph infections, bed sores and infected wounds as well as pre-treatment of surgical fields to reduce the likelihood of postoperative infection.

Figure 12:
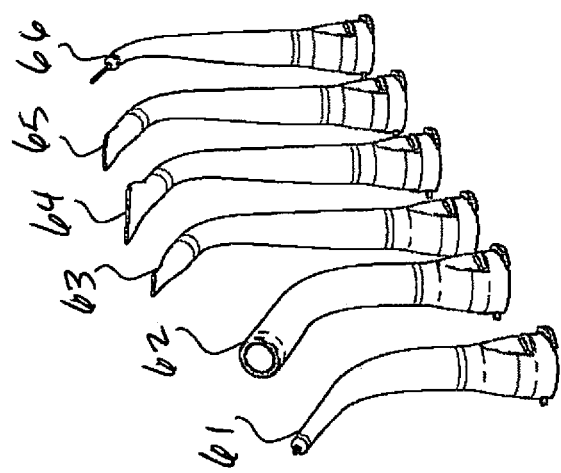
FIG. 12 illustrates a perspective view of several disposable tips that are used with an axial emitter.
Figure 13:
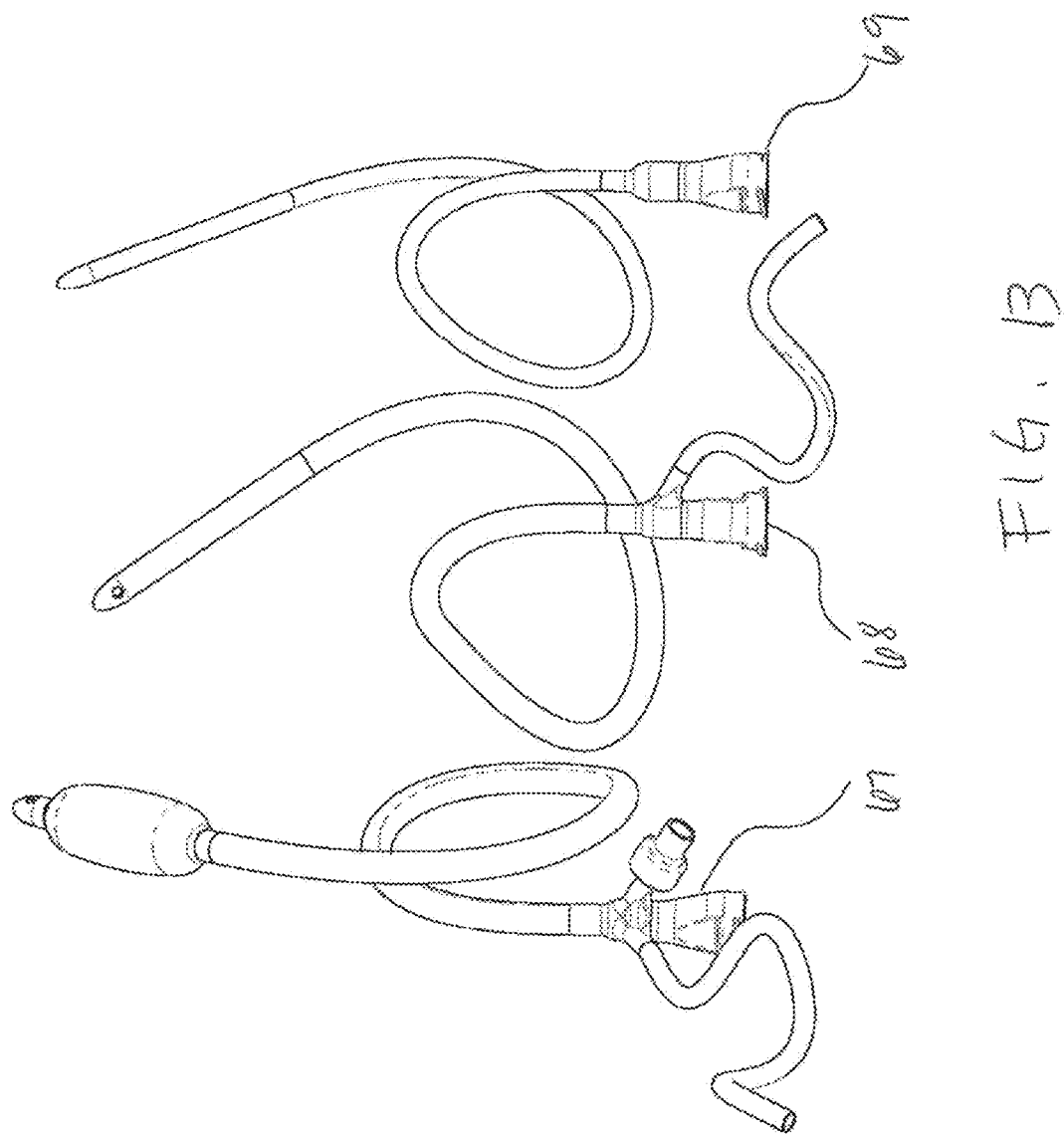
FIG. 13 illustrates a perspective view of several more disposable tips that are used with an axial emitter.

The tip 19 may instead be removable from the emitter head 12 and therefore disposable, as shown in FIGS. 6, 8A-B, 9, 11A-B, 12 and 13. The removable tip 19b can be configured to emit light in nearly any shape of beam spot, where a beam spot is the shape of the light as it intersects the surface. The removable tip 19b can be configured to be a fixed shape, flexible and resilient, or bendable into a static position. The removable tip 19b can be curved, straight, long or short length, thin or wide width, depending on the application. For insertion into body lumen, such as for catheterization, the tip may have a silicone balloon that may be inflated to increase the size of the cavity. See tip 67 in FIG. 13. FIGS. 12 and 13 illustrates several removable tips 61-69. Tip 61 is short single tip providing a concentrated beam useful for small areas and shallow cavities.

Tip 62 is a large round tip, useful for a larger area such as whole tooth surface. It is used mainly for polymer curing applications and broad surface treatments. Tip 63 is a thin flat tip, useful for periodontal treatments or hyponychial/nail-beds treatments in fingernails and toenails. Tip 64 is a wide flat tip, useful for dermatological treatments. Tip 65 is a wide rounded tip, also useful for dermatological treatments. Tip 66 is a long narrow tip providing a concentrated beam useful for small constricted areas and deep cavities, such as root canals. Tip 67 is useful as a foley catheter. Tip 68 is useful as a central venous system catheter. Tip 69 is useful as a flexible light tube that can be inserted within the lumen of either catheter to kill pathogens. Removable tips can rotate about the longitudinal axis of the handle 11 to help direct the light where desired.

FIGS. 6, 7, 8A and 8B show one embodiment of an emitter head 12 and a tip 19b removable therefrom. A treatment LED 20 is in electrical communication with a controller module 23. For LEDs that get hot during operation, optionally a heat sink 48 may be in communication with the treatment LED 20. FIGS. 9, 10, 11A and 11B show one embodiment of an emitter head 12 and a tip 19b removable therefrom. A proximity sensor 27 and a sensor controller 80 are disposed adjacent to a tracking light 21 and a task light 22 so that they illuminate the treated surface that the energy emitted through the emission aperture 26 illuminates. The sensor may be covered by a sensor cover 49. A treatment LED 20 is in electrical communication with a controller module 23. One or more lenses may be placed inline with the treatment LED, such as spherical lenses 81, to shape or manipulate the emitted energy. The sensor controller 80 is electrically connected to the emitter controller 23 and battery 15 in the handle 11 by attaching the wiring harness 44 to the connector 42 and a mated connector in the handle (not shown). Optionally a heat sink 48 may be in communication with the treatment LED 20.

In applications where the UV light is directed other than perpendicular to the longitudinal axis of the handle 11, the device can emit energy from the end of the tip to sanitize or sterilize a tooth; treat gum tissue infections, in particular peri-implantitis; treat the internal portion of a endodontically treated tooth prior to root canal obturation; and to treat foley catheter infection as well as bacterial and yeast based vaginitis.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

We claim:

1. A hand-held device for delivering light to a surface in a cavity of a patient's body, the device comprising:
    a. a handpiece having a longitudinal axis, the handpiece further comprising:
        i. a first end that mates with a first emitter head, wherein the first emitter head is sized to be placed in the patient's mouth;
        ii. a display;
        iii. a battery; and
        iv. a second end that mates with a base;
    b. the first emitter head removably mated to the first end of the handpiece, the first emitter head further comprising:
        i. a first LED for emitting UV-C energy;
        ii. a second LED for emitting visible light;
        iii. a sensor that triggers the prohibition of the emission of UV-C energy;
        iv. a memory device for storing a first set of operational parameters; and
        v. a control module in communication with the first and second LEDs, the sensor, the memory, the display and the battery; and
    c. a base connectable to the handpiece and connected to mains power for recharging the battery when the handpiece is connected to the base.

2. The device of claim 1 further comprising a second emitter head removably mated to the first end of the handpiece when the first emitter head has been removed and wherein the second emitter head is sized to be placed in the patient's mouth, the second emitter head further comprising:
    a. a third LED for emitting UV energy;
    b. a fourth LED for emitting visible light;
    c. a second sensor that triggers the prohibition of the emission of UV energy a second memory device for storing a first second set of operational parameters; and
    d. a second control module in communication with the third and fourth LEDs, the second sensor, the second memory, the display and the battery.

3. The device of claim 1 further comprising a tip integral with the first emitter head, the tip having a longitudinal axis co-axial with the longitudinal axis of the handpiece, wherein the tip is configured to direct UV-C energy perpendicular to the longitudinal axis of the handpiece.

4. The device of claim 1 further comprising a removable tip mated to the first emitter head, the removable tip for directing the UV-C energy to a desired location.

5. The device of claim 1 wherein the sensor is triggered to prohibit the emission of UV-C energy upon one or more of a predetermined proximity to a surface, cessation of motion, or expiration of a predetermined time period.

6. The device of claim 1 wherein the display is an auto-rotating alphanumeric graphic display further comprising an accelerometer and a gyroscope.

7. The device of claim 1 wherein the sensor is a LIDAR proximity sensor.

8. The device of claim 1 wherein the emitter head is in communication with a remote store of treatment protocols.

9. The device of claim 1 wherein the sensor is an ambient light proximity sensor.

10. A hand-held device for delivering light to a surface in a patient's mouth, the device comprising:
    a. a handpiece having a longitudinal axis, the handpiece further comprising:
        i. a first end that mates with an emitter head;
        ii. a display;
        iii. a battery; and
        iv. a second end that mates with a base;
    b. the emitter head having a proximate end that mates with the first end of the handpiece;
    c. the emitter head having a distal end that further comprises:
        i. a first LED for emitting UV-C energy disposed near the distal end;
        ii. a lens through which the UV-C energy is emitted;
        iii. a second LED for emitting visible light that tracks where the UV-C energy is directed disposed next to the first LED;
        iv. a third LED for emitting visible light disposed between the distal end and the proximate end of the emitter head for providing task lighting;
        v. a proximity sensor disposed between the third LED and the first LED;
        vi. a memory device for storing operational parameters; and
        vii. a control module in communication with the first, second, and third LEDs, the proximity sensor, the memory, the display and the battery;
        viii. wherein the lens and first LED are configured to direct UV-C energy perpendicular to the longitudinal axis of the handpiece; and
    d. a base connectable to the handpiece and connected to mains power for recharging the battery when the handpiece is connected to the base.

11. The device of claim 10 wherein the proximity sensor is a time-of-flight LIDAR device.

12. The device of claim 10 wherein the proximity sensor:
    a. triggers the prohibition of the emission of UV-C energy under certain conditions, wherein the certain conditions are one or more of a predetermined proximity to a surface, cessation of motion, or expiration of a predetermined time period; and b. causes the control module to make adjustments to the emitted UV-C light, wherein such adjustments are one or more of the intensity of the UV-C light, the rate of change of intensity, the duration of the emission, based on a predetermined proximity to a surface, cessation of motion, or expiration of a predetermined time period.

13. The device of claim 10 wherein the emitter head is in communication with a remote store of treatment protocols.

14. The device of claim 10 further comprising up to a fourth, a fifth, or a sixth LED for emitting visible light, each of the fourth, a fifth, or sixth LEDs disposed between the distal end and the proximate end of the emitter head.

15. The device of claim 10 wherein the sensor is an ambient light proximity sensor.

16. A hand-held device for delivering light to a surface in a cavity of a patient's body, the device comprising:
  a. a handpiece having a longitudinal axis, the handpiece further comprising:
    i. a first end that mates with a first emitter head, wherein the first emitter head is sized to be placed in the patient's mouth;
    ii. a display; and
    iii. a battery; and
  b. the first emitter head removably mated to the first end of the handpiece, the first emitter head further comprising:
    i. a first LED for emitting UV-C energy;
    ii. a sensor that triggers the prohibition of the emission of UV-C energy;
    iii. a memory device for storing a first set of operational parameters; and
    iv. a control module in communication with the first LED, the sensor, the memory, the display and the battery;
  wherein the first emitter head is preprogrammed with the first set of operational parameters.

17. The device of claim 16 wherein the sensor is triggered to prohibit the emission of UV-C energy upon one or more of a predetermined proximity to a surface, cessation of motion, or expiration of a predetermined time period.

18. The device of claim 16 further comprising a second LED for emitting visible light.

19. A hand-held device for delivering light to a surface in a cavity of a patient's body, the device comprising:
  a. a first emitter head removably mated to a handpiece, the first emitter head further comprising:
    i. a first LED for emitting UV-C energy;
    ii. a sensor that triggers the prohibition of the emission of UV-C energy;
    iii. a memory device for storing a first set of operational parameters; and
    iv. a control module in communication with the first LED, the sensor, the memory, the display and the battery;
  wherein the first emitter head is preprogrammed with the first set of operational parameters.

20. The device of claim 19 further comprising a second LED for emitting visible light.

* * * * *